(12) United States Patent
Lloyd

(10) Patent No.: US 8,991,400 B2
(45) Date of Patent: Mar. 31, 2015

(54) EMERGENCY TRANSPORT BACK SUPPORT APPARATUS AND METHOD

(76) Inventor: Richard E. Lloyd, Hardy, AR (US)

( * ) Notice: Subject to any disclaimer, the term of this patent is extended or adjusted under 35 U.S.C. 154(b) by 1002 days.

(21) Appl. No.: 11/657,344

(22) Filed: Jan. 24, 2007

(65) Prior Publication Data

US 2008/0173316 A1 Jul. 24, 2008

(51) Int. Cl.
*A61F 5/37* (2006.01)
*A61F 5/00* (2006.01)
*A61F 5/30* (2006.01)
*A61G 1/04* (2006.01)

(52) U.S. Cl.
CPC .... *A61F 5/30* (2013.01); *A61G 1/04* (2013.01)
USPC .......................................... 128/870; 602/19

(58) Field of Classification Search
USPC .................................... 602/6, 8, 19
See application file for complete search history.

(56) References Cited

U.S. PATENT DOCUMENTS

| | | | |
|---|---|---|---|
| 3,309,714 A | 3/1967 | Porten | |
| 3,403,676 A | 10/1968 | Gibbons | |
| 3,631,854 A | 1/1972 | Fryer | |
| 3,643,656 A | 2/1972 | Young et al. | |
| 3,913,571 A * | 10/1975 | Bayer et al. | 602/8 |
| 4,019,506 A * | 4/1977 | Eschmann | 602/8 |
| 4,231,356 A * | 11/1980 | Usukura | 602/8 |
| 4,475,543 A | 10/1984 | Brooks et al. | |
| 4,793,330 A * | 12/1988 | Honeycutt et al. | 602/8 |
| 4,817,590 A | 4/1989 | Stancik, Jr. | |
| 5,176,621 A * | 1/1993 | Schulz | 602/8 |
| 5,285,797 A * | 2/1994 | Zeller | 5/628 |
| 5,378,223 A | 1/1995 | Grim et al. | |
| 5,390,682 A | 2/1995 | Iams | |
| 5,437,614 A | 8/1995 | Grim | |
| 5,452,728 A | 9/1995 | Iams | |
| 5,632,723 A * | 5/1997 | Grim | 602/19 |
| 5,954,676 A | 9/1999 | Kramer, III | |
| 6,055,988 A * | 5/2000 | Perisho | 128/869 |
| 6,358,220 B1 * | 3/2002 | Langen et al. | 602/8 |
| 2004/0077979 A1 * | 4/2004 | Karason et al. | 602/3 |
| 2005/0033207 A1 | 2/2005 | Anders | |
| 2006/0282030 A1 * | 12/2006 | Martin et al. | 602/8 |

* cited by examiner

*Primary Examiner* — Victoria J Hicks

(57) ABSTRACT

A back support apparatus intended for use during emergency transport of a patient suffering an actual or suspected spine injury is disclosed. The device provides a solid support for the arched portion of the spine that molds to the shape of the individual patient's back. The device comprises a bag or other container into which a solid curable material and a liquid activator are introduced, which is then placed beneath the patient's spine on a back board or like support. The device may be deployed quickly without the need for additional straps, belts, or the like, and may be treated as disposable due to its low cost.

5 Claims, 2 Drawing Sheets

EMERGENCY TRANSPORT BACK SUPPORT APPARATUS AND METHOD

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to back supports for use during the emergency transport of patients to a medical facility following an actual or suspected spinal injury, and in particular relates to such supports that conform to the precise shape of an individual patient's back for support of the arched region of the spine.

2. Brief Description of the Related Art

Upon arrival at an accident scene, the first task of an emergency medical technician (EMT) or other first responder is to assess the condition of the injured person or persons. If a back or neck injury is indicated or suspected as a result of this assessment, the responder must take great care in loading the patient into an ambulance or other vehicle in order to avoid additional injury to the patient during loading or during transport to a medical facility. The typical practice is to place a cervical collar around the neck of the patient to hold the neck in place, and then the patient is transferred to a rigid back board and secured in place with straps. This prevents the patient from being moved or jostled during transport.

Although the cervical collar and back board do provide some support and protection for the patient, the spinal column is not perfectly straight, and thus the arched portions of the spine are not supported by the flat back board during transport. Each bump encountered by the ambulance or other vehicle during the transportation process will result in a deflection of the portion of the spine that is arched above the back board. Tests conducted by the inventor of the present invention have demonstrated that deflections due to railroad tracks, pot holes, rough gravel roads, and sudden dips in major highways may cause deflection in the arched area of the spine by as much as 0.35 inches. This deflection and repeated deflections may result in a furtherance of damage to the spinal column in a patient that has suffered a spinal column injury, and in the worst cases may result in permanent paralysis, where full support of the spinal column might have prevented the injury from being increased.

The prior art includes several efforts to provide for immobilization of various body parts during transport, although none of these solutions are entirely satisfactory for the application described above. For example, U.S. Patent Publication No. 2005/0033207 to Anders teaches an apparatus to immobilize an injured body part, such as the head/neck or a limb, which includes one or more flexible bags. With the apparatus placed in proximity to an injured body part, two precursor agents are mixed in the bags to produce a reaction that results in a foam that fills the bags. The foam solidifies in a short time to provide a solid support for the injured body part.

Although the Anders specification includes the assertion that the Anders device may be used to provide full cervical spine immobilization, the device actually provides only head immobilization without solid support for the arched portion of the spine when a patient is secured to a back board. In addition, the use of foam or other air-inflation techniques is not desirable for support of the spine because of the possibility of a lifting affect on an injured area of the spine. This may cause localized pressure that could result in further injury to a damaged spinal cord.

The prior art also includes several types of back supports that are intended to conform to the shape of the spine, although none are intended for immobilization of a patient during transport. U.S. Pat. No. 4,475,543 to Brooks et al. teaches a back brace comprising a wide elastic belt and a pouch at the spine. The pouch contains a bag that may be filled with a curable foam, which conforms to the shape of the patient's back and hardens in place. Similarly, U.S. Pat. Nos. 5,437,614 and 5,632,723 to Grim teach a back support with one or more bag inserts that contains a urethane pre-polymer matrix. Water is injected into the bags, which results in a hardening of the matrix into a shape that conforms to the wearer. Each of these devices are intended to provide support during walking, not for securing the spine in an immobilized state during transport of a patient with an actual or suspected spinal injury.

In addition to the limitations already noted, it may be seen that each of the prior art devices are rather complex, requiring various adhesives, straps, belts, or the like to hold them in place. The proper placement of such devices will require a significant amount of time, which would delay transport of a patient to a medical facility during an emergency situation. Since even a few seconds may be critical to a patient's survival and recovery, such devices are not practical for emergency response applications. The limitations of the prior art are overcome by the present invention as described below.

BRIEF SUMMARY OF THE INVENTION

The present invention is directed to a back support apparatus and method that provides complete, firm support for a patient's spinal column during transport. The invention comprises a bag or other flexible container and a solid (i.e., non-foaming) curable material, such as the various quick-curing varieties of plaster of Paris. An activator is introduced to the solid curable material, and the bag is placed at a position beneath the arched area of the patient's back on a conventional back board. Once the material cures, the patient's back will be fully supported during loading of the patient into an ambulance or other vehicle and during transport to a medical facility. Because there is no foam or gas injection as in some prior art devices, the contours of the individual patient's spine will be supported without applying any localized pressure to the injured area. Also, since the device is inexpensive to manufacture, it may be disposed of after each use. The liquid activator, preferably water, may be included in an easily ruptured inner bag within the main bag of the device, or may be packaged externally and inserted into the bag in the field in alternative embodiments.

It is therefore an object of the present invention to provide for a back support that may be used during the emergency transport of a patient suffering from an actual or suspected spinal cord injury.

It is a further object of the present invention to provide for a back support that forms to fit the curvature of a patient's spine, thereby providing complete support when a patient is situated on a backboard during loading into an ambulance or other vehicle and during transport to a medical facility.

It is also an object of the present invention to provide a back support that is inexpensive to manufacture.

It is also an object of the present invention to provide a back support that may be easily and quickly deployed in the field during an emergency response situation.

It is also an object of the present invention to provide a back support with a minimum of necessary additional training for use by emergency responders employing the device.

These and other features, objects and advantages of the present invention will become better understood from a consideration of the following detailed description of the preferred embodiments and appended claims in conjunction with the drawings as described following:

DETAILED DESCRIPTION OF THE PREFERRED EMBODIMENTS

Figure 1:
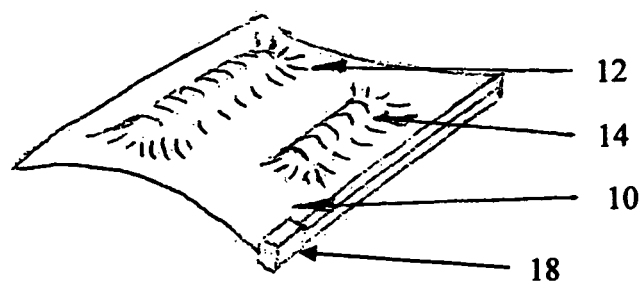
FIG. 1 is a perspective view of a first preferred embodiment of the present invention prior to use.

With reference to FIG. 1, a first preferred embodiment of the present invention may now be described. Bag 10 may be formed of polypropylene plastic or other such material as sufficient to contain the other components as described herein and be sufficiently flexible to allow for curing in the shape of a patient's arched spinal column. In one embodiment, bag 10 may simply be a household reclosable bag with sliding lock 18, as commonly used for freezing or storing foods. Such bags include the Ziploc brand freezer bags sold by S.C. Johnson & Son, Inc. of Racine, Wis. A preferred capacity for bag 10 is about one quart.

Further according to the first preferred embodiment of FIG. 1, bag 10 contains solid curable material 12, which may preferably be in the form of a dry powder. In one preferred embodiment, solid curable material 12 may be one of the various forms of quick-setting plaster of paris. Plaster of paris is a common building and sculpturing material based on calcium sulfate hemihydrate, which has been used for various purposes since ancient times. Quick-curing forms of plaster of paris are commercially available that cure to a solid in approximately 4-6 minutes, and form a soft paste within about 30 seconds of mixing. Bag 10 also contains inner bag 14, which is formed of a thin plastic or other material that may be ruptured upon the application of pressure. Inner bag 14 contains an liquid activator agent that operates to cure solid curable material 12 when it is intermixed with solid curable material 12. A preferred capacity for inner bag 14 is about 8 ounces, and the preferred liquid activator material is water. In order to activate the device, inner bag 14 is preferably ruptured by placing bag 10 on a hard surface and applying pressure to inner bag 14 with the heel of the hand. Inner bag 14 then ruptures, and the liquid activator within inner bag 14 may be combined with solid curable material 12 by manually kneading bag 10 until the two components are thoroughly mixed. If quick-setting plaster of paris is used as solid curable material 12, a soft paste will be formed after about 30 seconds of mixing in this manner.

Figure 2:
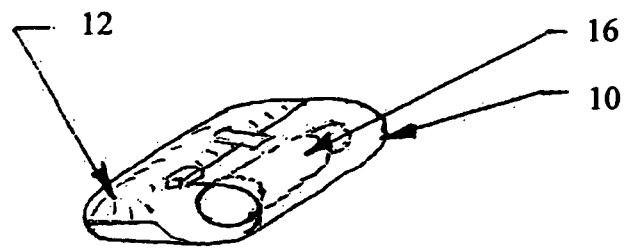
FIG. 2 is a perspective view of a second preferred embodiment of the present invention prior to use.

With reference to FIG. 2, a second preferred embodiment of the present invention may now be described. In this embodiment, bag 10 still contains solid curable material 12 as described above with respect to the preferred embodiment of FIG. 1. In this case, however, there is no inner bag 14, and the liquid activator agent is stored outside of bag 10 in bottle 16 or another like container. Bottle 16 preferably has a capacity of about 8 ounces. Bottle 16 may preferably be packaged with bag 10, such as shown in FIG. 2 where bag 10 is folded over bottle 16 and secured with a removable adhesive strip. This arrangement facilitates quick access to all needed materials during an emergency response situation. In order to deploy the device, bag 10 is opened at lock 18, and the liquid activator is poured or squirted into bag 10 from bottle 16. Lock 18 is then closed and bag 10 may be manually kneaded in order to thoroughly mix solid curable material 12 with the liquid activator.

Figure 3:
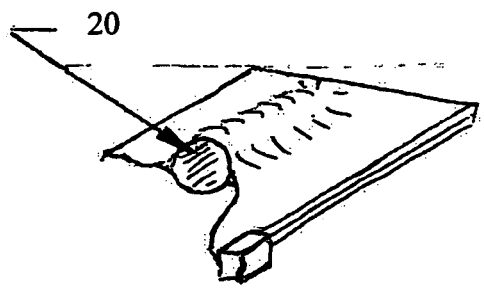
FIG. 3 is a perspective view of a preferred embodiment of the present invention when ready to be deployed with respect to a patient.

Once the liquid activator is added to solid curable material 12 in bag 10, both the first and second preferred embodiments described above are preferably deployed in a similar manner. Solid curable material 12, when mixed with the liquid activator, will begin to form a thick, soft, homogenous paste. This paste is then manually formed into the rough shape of cylindrical roll 20 within bag 10, as depicted in FIG. 3. Preferably, roll 20 is about two inches in diameter. If quick-setting plaster of paris is used as curable material 12, this step should be completed in around 30 seconds from mixing since the material will begin to harden if more time is taken. If bag 10 includes lock 18, then roll 20 should preferably be formed parallel to the direction of lock 18; in this manner, the circumstance of lock 18 impinging upon the patient's spine longitudinally is avoided. Bag 10 may optionally be opened at lock 18 to allow any air to escape that has entered bag 10, particularly where lock 18a was opened to add the liquid activator. The bag is then resealed at lock 18 and is ready for use.

Figure 4:
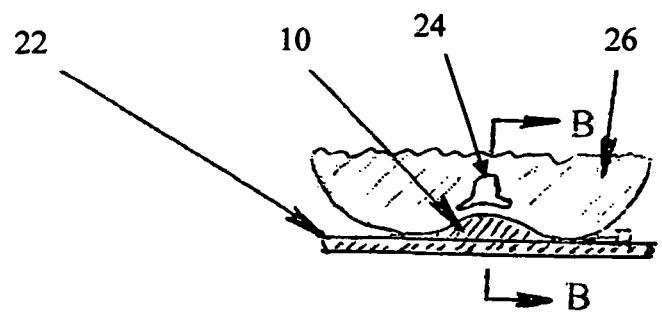
FIG. 4 is a longitudinal elevational view in cross-section of a patient depicting a preferred embodiment of the present invention positioned beneath the patient's spine on a back board.
Figure 5:
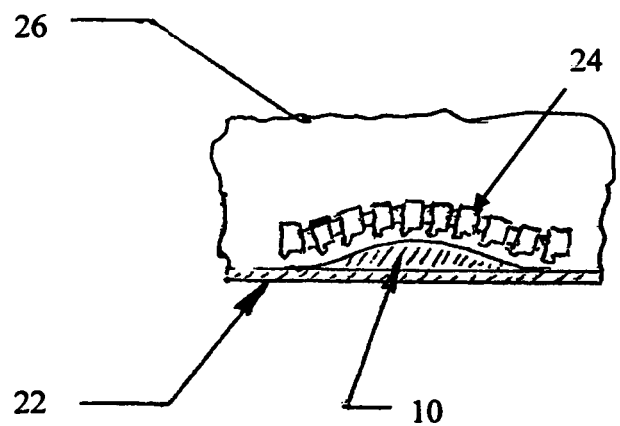
FIG. 5 is a side elevational view in cross-section taken along section line B-B of FIG. 4.

Referring now to FIGS. 4 and 5, the deployment of the device after the formation of roll 20 may be described. Bag 10 is placed on back board 22 under the arched portion of the patient's spine 24, such that when patient 26 is placed on back board 22, bag 10 will conform to the shape of spine 24. It may be seen that since no pressure is introduced into bag 10 during this use, there is no localized pressure being applied to spine 24. The patient is then strapped to the back board in the conventional manner, and may be loaded into an ambulance or other vehicle for emergency transport. Due to the quick curing time of the material preferably employed, it will be seen that by the time transport begins the material will likely be fully cured and solid, thereby providing a firm support for spine 24 even as the vehicle transporting patient 26 passes over bumpy roads, railroad tracks, or the like. If desirable, the temperature of the liquid activator may be increased, which may further decrease the curing time in materials such as quick-setting plaster of paris.

The present invention has been described with reference to certain preferred and alternative embodiments that are intended to be exemplary only and not limiting to the full scope of the present invention as set forth in the appended claims.

What is claimed is:

1. A method of stabilizing a patient's spine during emergency transport, comprising:

(a) securing the patient in a supine position to a backboard, wherein the backboard comprises a flat surface longer and wider than the patient;
(b) introducing a liquid activator to a solid curable material within a flexible container;
(c) mixing the liquid activator and the solid curable material by kneading the flexible container until the liquid activator and the solid curable material form a paste;
(d) forming the paste within the flexible container into a cylindrical roll; and
(e) while securing the patient to the backboard in a supine position, inserting the flexible container onto the backboard in a position such that the cylindrical roll is fitted within a space formed by the backboard and an arched portion of the patient's lower spine.

2. The method of claim 1, wherein said introducing a liquid activator to a solid curable material within a flexible container step comprises a step of rupturing an inner container within said flexible container.

3. The method of claim 1, wherein said introducing a liquid activator to a solid curable material within a flexible container step comprises a step of opening the flexible container at a reclosable opening and dispensing the liquid activator from a liquid container.

4. The method of claim 1, wherein the solid curable material comprises quick-setting gypsum plaster, the liquid activator comprises water, and said mixing the liquid activator and the solid curable material by kneading the flexible container until the liquid activator and the solid curable material form a paste step and the forming the paste within the flexible container into a cylindrical roll step are completed within 30 seconds of said introducing a liquid activator to a solid curable material within a flexible container step.

5. The method of claim 1, further comprising a step of heating the liquid activator prior to said introducing a liquid activator to a solid curable material within a flexible container step.

* * * * *